US008969497B2

(12) United States Patent
Handa et al.

(10) Patent No.: US 8,969,497 B2
(45) Date of Patent: Mar. 3, 2015

(54) METHOD FOR PRODUCING WATER-ABSORBENT RESIN, AND WATER-ABSORBENT RESIN OBTAINED BY SAME

(75) Inventors: Masayoshi Handa, Himeji (JP); Junichi Takatori, Himeji (JP)

(73) Assignee: Sumitomo Seika Chemicals Co., Ltd., Kako-gun (JP)

( * ) Notice: Subject to any disclaimer, the term of this patent is extended or adjusted under 35 U.S.C. 154(b) by 0 days.

(21) Appl. No.: 14/241,595

(22) PCT Filed: Aug. 23, 2012

(86) PCT No.: PCT/JP2012/071347
§ 371 (c)(1),
(2), (4) Date: Feb. 27, 2014

(87) PCT Pub. No.: WO2013/031654
PCT Pub. Date: Mar. 7, 2013

(65) Prior Publication Data
US 2014/0194574 A1 Jul. 10, 2014

(30) Foreign Application Priority Data

Aug. 30, 2011 (JP) .................................. 2011-187452

(51) Int. Cl.
C08F 2/14 (2006.01)
C08F 8/00 (2006.01)
B01J 20/26 (2006.01)
C08F 2/20 (2006.01)
C08F 2/32 (2006.01)
C08J 3/24 (2006.01)
A61L 15/60 (2006.01)
B01J 20/30 (2006.01)
C08F 120/06 (2006.01)

(52) U.S. Cl.
CPC .................. *C08F 120/06* (2013.01); *C08F 2/20* (2013.01); *C08F 2/32* (2013.01); *C08J 3/245* (2013.01); *A61L 15/60* (2013.01); *B01J 20/261* (2013.01); *B01J 20/3085* (2013.01); *Y10S 526/93* (2013.01)
USPC ........... 526/201; 526/203; 526/209; 526/240; 526/317.1; 526/930; 525/329.7

(58) Field of Classification Search
USPC .............. 526/201, 203, 209, 930, 240, 317.1; 525/329.7
See application file for complete search history.

(56) References Cited

U.S. PATENT DOCUMENTS

| 4,683,274 | A  | 7/1987  | Nakamura et al. |
| 5,475,062 | A  | 12/1995 | Ishizaki et al. |
| 2005/0209352 | A1 | 9/2005 | Dairoku et al. |
| 2009/0182092 | A1 | 7/2009 | Yokoyama et al. |

FOREIGN PATENT DOCUMENTS

| JP | 57-158210 A | 9/1982 |
| JP | 61-87702 A | 5/1986 |
| JP | 6-220227 A | 8/1994 |
| JP | 8-27278 A | 1/1996 |
| JP | 9-136966 A | 5/1997 |
| JP | 2000-128907 A * | 5/2000 |
| JP | 2001-96151 A | 4/2001 |
| JP | 2010-158667 A | 7/2010 |
| WO | WO 2005/075070 A1 | 8/2005 |
| WO | WO 2007/126002 A1 | 11/2007 |

OTHER PUBLICATIONS

Online machine translation of JP 2010-158667A; pub. date: Jul. 2010.*
Online machine translation of JP 2000-128907A; pub. date: May 2000.*
International Search Report issued Sep. 18, 2012 in PCT/JP2012/071347.
U.S. Appl. No. 14/369,580, filed Jun. 27, 2014, Matsushita, et al.

* cited by examiner

*Primary Examiner* — Fred M Teskin
(74) *Attorney, Agent, or Firm* — Oblon, McClelland, Maier & Neustadt, L.L.P.

(57) ABSTRACT

A method for producing a water-absorbent resin including the step of subjecting a water-soluble ethylenically unsaturated monomer to a reversed phase suspension polymerization in a petroleum hydrocarbon dispersion medium in the presence of a radical polymerization initiator and a dispersion stabilizer, wherein the method is characterized by the use of an ether-ester type nonionic surfactant as the dispersion stabilizer, and a water-absorbent resin obtained by the method, wherein the water-absorbent resin has a water-retention capacity of saline solution of 25 g/g or more, a water-absorption rate of saline solution of 50 seconds or less, and a flow index under moisture absorption of 70% or more. According to the method of the present invention, a water-absorbent resin having high water-retention capacity, excellent water-absorption rate, and further having excellent flowability under moisture absorption can be produced. The water-absorbent resin having the specified physical properties as described above can enhance properties of hygienic materials, and the resin can be suitably used in the production of the hygienic materials.

8 Claims, 1 Drawing Sheet

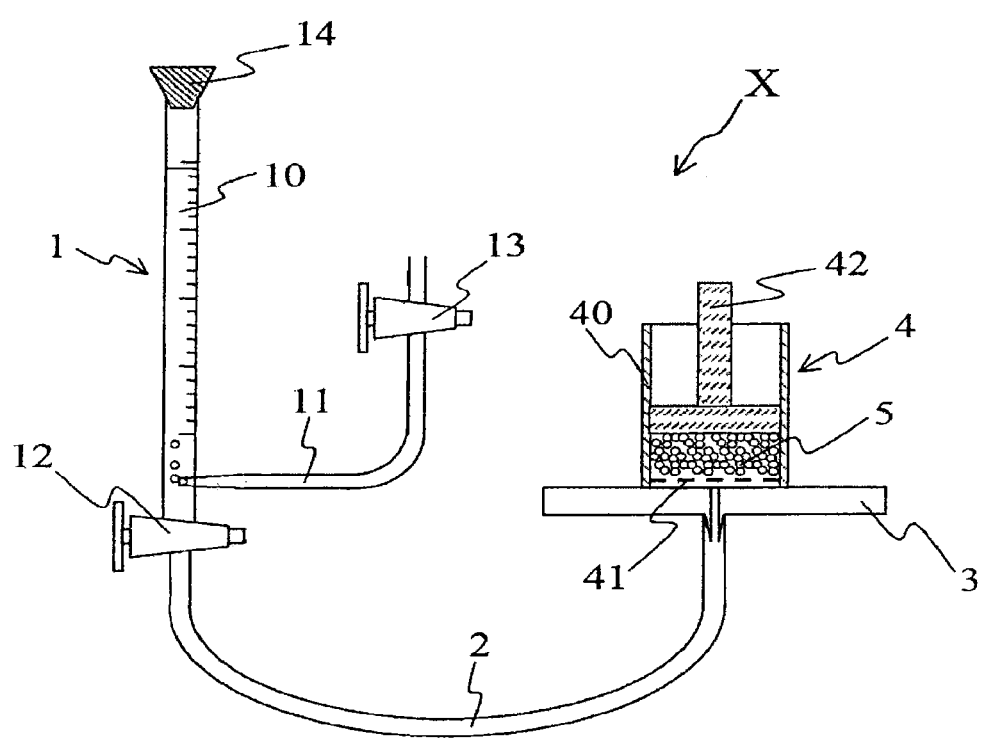

METHOD FOR PRODUCING WATER-ABSORBENT RESIN, AND WATER-ABSORBENT RESIN OBTAINED BY SAME

TECHNICAL FIELD

The present invention relates to a method for producing a water-absorbent resin, and a water-absorbent resin obtained thereby. More specifically, the present invention relates to a method for producing a water-absorbent resin used in various fields, including hygienic materials such as sanitary napkins, incontinence pads and disposable diapers, horticultural materials such as water retaining materials and soil improvers, and industrial materials such as water blocking materials and dew catchers, and a water-absorbent resin obtained thereby.

BACKGROUND ART

Water-absorbent resins have been widely used in various fields, including hygienic materials such as sanitary napkins, incontinence pads and disposable diapers, horticultural materials such as water retaining materials and soil improvers, and industrial materials such as water blocking materials and dew catchers. As the water absorbent resins, for example, hydrolysates of starch-acrylonitrile graft copolymers, neutralized products of starch-acrylic acid graft copolymers, saponified products of vinyl acetate-acrylic acid ester copolymers, crosslinked products of partially neutralized polymers of acrylic acid, and the like have been known.

Usually, the water-absorbent resin usable in an absorbent material of hygienic material applications has been demanded to be excellent in various properties such as water-retention capacity (water-absorption capacity), water-absorption capacity under load, water-absorption rate, and gel strength. So far, techniques remarking, for example, high water-retention capacity, excellent water-absorption rate and the like among the above-mentioned properties have been studied.

In addition, recently, water-absorbent resins have been demanded to be excellent in properties suitable in the production of hygienic materials, for example, flowability under moisture absorption. Since the water-absorbent resins absorb moisture in the atmosphere, and are likely to cause adhesion to a metal plate or aggregation between particles, a solid adhesion is likely to be formed in a production machine of hygienic materials (for example, a drum former), so that frequent cleanings would be necessitated, thereby making it likely to lower the productivity of the hygienic materials. Also, when a water-absorbent resin in an aggregated state due to moisture absorption is used in the hygienic materials, there is a possibility of worsening the properties of the hygienic materials such as an increase in leakage or re-wet caused by gel blocking.

Conventionally, in view of the above-mentioned problems, a variety of techniques have been proposed in order to improve various properties of the water-absorbent resin. For example, a method including adding an organic carboxylic acid ester of a polyvalent alcohol to a water-absorbent resin, and heat-treating the mixture (see, Patent Publication 1), a method including adding a ketal compound, an acetal compound or an alkyl ether of a polyvalent alcohol to a water-absorbent resin, and heat-treating the mixture (see, Patent Publication 2), a method including adding a specified silicone surfactant to a water-absorbent resin, and surface-treating the water-absorbent resin (see, Patent Publication 3), a method including adding a polyvalent metal to a water-absorbent resin, and surface-treating the water-absorbent resin (see, Patent Publication 4) and the like have been reported. In addition to the above, as a method using a hydrophobic compound such as a surfactant, in which a reversed phase suspension polymerization is employed as a core reaction, a method using an oil-soluble cellulose ester or cellulose ether as a dispersant (see, Patent Publication 5), a method using a sucrose fatty acid ester (see, Patent Publication 6), and the like have been reported.

PRIOR ART REFERENCES

Patent Publications

Patent Publication 1: Japanese Patent Laid-Open No. Hei-6-220227
Patent Publication 2: Japanese Patent Laid-Open No. Hei-8-27278
Patent Publication 3: Japanese Patent Laid-Open No. Hei-9-136966
Patent Publication 4: Japanese Patent Laid-Open No. 2001-96151
Patent Publication 5: Japanese Patent Laid-Open No. Sho-57-158210
Patent Publication 6: Japanese Patent Laid-Open No. Sho-61-87702

SUMMARY OF THE INVENTION

Problems to be Solved by the Invention

However, water-absorbent resins which can satisfy properties suitable for use in hygienic materials, especially those that can satisfy water-retention capacity, water-absorption rate and flowability under moisture absorption at the same time have not been obtained in the conventional techniques.

An object of the present invention is to provide a method for producing a water-absorbent resin having a high water-retention capacity and an excellent water-absorption rate, and further having an excellent flowability under moisture absorption as the properties suitable for a water-absorbent material usable in hygienic materials, and a water-absorbent resin obtained thereby.

Means to Solve the Problems

The present invention relates to:
[1] a method for producing a water-absorbent resin, comprising the step of subjecting a water-soluble ethylenically unsaturated monomer to a reversed phase suspension polymerization in a petroleum hydrocarbon dispersion medium in the presence of a radical polymerization initiator and a dispersion stabilizer, wherein the method is characterized by the use of an ether-ester type nonionic surfactant as the dispersion stabilizer; and
[2] a water-absorbent resin obtained by the method of the above [1], wherein the water-absorbent resin has a water-retention capacity of saline solution of 25 g/g or more, a water-absorption rate of saline solution of 50 seconds or less, and a flow index under moisture absorption of 70% or more.

Effects of the Invention

According to the method of the present invention, a water-absorbent resin having a high water-retention capacity and an excellent water-absorption rate, and further having an excellent flowability under moisture absorption can be produced. The water-absorbent resin having the specified properties as described above can enhance various properties of hygienic materials and can also be suitably used in the production of the hygienic materials.

BRIEF DESCRIPTION OF THE DRAWINGS

FIG. A schematic view showing an outline constitution of an apparatus for measuring a water-absorption capacity under load.

MODES FOR CARRYING OUT THE INVENTION

The method for producing a water-absorbent resin of the present invention is characterized by the use of an ether-ester type nonionic surfactant as a dispersion stabilizer in the method including subjecting a water-soluble ethylenically unsaturated monomer to a reversed phase suspension polymerization in a petroleum hydrocarbon dispersion medium in the presence of a radical polymerization initiator and a dispersion stabilizer.

The ether-ester type nonionic surfactant includes, but not limited to, for example, polyoxyethylene cetyl ether stearate, polyoxyethylene stearyl ether stearate, polyoxyethylene lauryl ether stearate, polyoxyethylene lauryl ether isostearate, polyoxyethylene glycerol monostearate, polyoxyethylene castor oil, polyoxyethylene hydrogenated castor oil, polyoxyethylene sorbitan triisostearate, polyoxyethylene sorbitan monooleate, polyoxyethylene sorbitan trioleate, polyoxyethylene sorbitan monolaurate, polyoxyethylene sorbitan monopalmitate, and the like.

Among them, the ether-ester type nonionic surfactant is preferably at least one member selected from the group consisting of polyoxyethylene cetyl ether stearate, polyoxyethylene stearyl ether stearate, polyoxyethylene lauryl ether stearate and polyoxyethylene lauryl ether isostearate, and more preferably polyoxyethylene cetyl ether stearate and polyoxyethylene stearyl ether stearate, from the viewpoint of dispersion stability of the water-soluble ethylenically unsaturated monomer. These surfactants may be used alone or in combination of two or more kinds.

The ether-ester type nonionic surfactant used in the present invention has an HLB value (Hydrophilic-Lipophilic Balance) of preferably from 2 to 11, more preferably from 3 to 9, and even more preferably from 4 to 7, from the viewpoint of increasing flowability under moisture absorption of the water-absorbent resin obtained, and obtaining a water-absorbent resin having an excellent water-absorption rate.

In addition, as the dispersion stabilizer, a polymeric dispersion agent may be used together with the above-mentioned ether-ester type nonionic surfactant. The polymeric dispersion agent to be used includes maleic anhydride-modified polyethylene, maleic anhydride-modified polypropylene, maleic anhydride-modified ethylene-propylene copolymer, maleic anhydride-modified EPDM (ethylene-propylene-diene terpolymer), maleic anhydride-modified polybutadiene, maleic anhydride-ethylene copolymer, maleic anhydride-ethylene-propylene copolymer, maleic anhydride-butadiene copolymer, oxidized polyethylene, ethylene-acrylic acid copolymer, ethyl cellulose, ethyl hydroxyethyl cellulose, and the like. Among them, maleic anhydride-modified polyethylene, maleic anhydride-modified polypropylene, maleic anhydride-modified ethylene-propylene copolymer, oxidized polyethylene, and ethylene-acrylic acid copolymer are preferred, from the viewpoint of dispersion stability of the water-soluble ethylenically unsaturated monomer. These polymeric dispersion agents may be used alone or in combination of two or more kinds.

The dispersion stabilizer is used in an amount of preferably from 0.05 to 10 parts by mass, more preferably from 0.1 to 8 parts by mass, and even more preferably from 0.2 to 5 parts by mass, based on 100 parts by mass of the water-soluble ethylenically unsaturated monomer, from the viewpoint of favorably keeping a dispersion state of the water-soluble ethylenically unsaturated monomer in the petroleum hydrocarbon dispersion medium, and obtaining a dispersion effect accounting to the amount used.

When the ether-ester type nonionic surfactant is used together with the polymeric dispersion agent, a mass ratio of the ether-ester type nonionic surfactant (A) to the polymeric dispersion agent (B), i.e. (A)/(B), of a total amount of the dispersion stabilizers is preferably from 95/5 to 10/90, more preferably from 80/20 to 20/80, and even more preferably from 70/30 to 30/70, from the viewpoint of favorably keeping a dispersion state of the water-soluble ethylenically unsaturated monomer in the petroleum hydrocarbon dispersion medium, and enhancing various properties of the water-absorbent resin described in the present invention. The amount of the ether-ester type nonionic surfactant when used together with the polymeric dispersion agent is preferably from 0.005 to 9.5 parts by mass, more preferably from 0.02 to 6.4 parts by mass, and even more preferably from 0.06 to 3.5 parts by mass, based on 100 parts by mass of the water-soluble ethylenically unsaturated monomer.

The water-soluble ethylenically unsaturated monomer used in the present invention includes, for example, (meth)acrylic acid (in the present specification, "acryl-" and "methacryl-" are together expressed as "(meth)acryl-"; hereinafter referred to the same) and salts thereof; 2-(meth)acrylamide-2-methylpropanesulfonic acid and salts thereof; nonionic monomers such as (meth)acrylamide, N,N-dimethyl (meth)acrylamide, 2-hydroxyethyl (meth)acrylate, N-methylol (meth)acrylamide, and polyethylene glycol mono(meth)acrylate; amino group-containing unsaturated monomers such as N,N-diethylaminoethyl (meth)acrylate, N,N-diethylaminopropyl (meth)acrylate and diethylaminopropyl (meth)acrylamide, and a quaternary compound thereof; and the like. These water-soluble ethylenically unsaturated monomers may be used alone or in combination of two or more kinds.

Among them, (meth)acrylic acid and salts thereof, (meth)acrylamide, N,N-dimethylacrylamide and the like are preferred, and (meth)acrylic acid and salts thereof are more preferred, from the viewpoint of being readily industrially available.

Incidentally, the above-mentioned water-soluble ethylenically unsaturated monomer may be used in the form of an aqueous solution, in order to elevate a dispersion efficiency in the petroleum hydrocarbon dispersion medium during the reversed phase suspension polymerization. The concentration of the above-mentioned monomer in the aqueous solution is, but not particularly limited to, usually 20% by mass or higher and a saturated concentration or lower, preferably from 25 to 70% by mass, and more preferably from 30 to 55% by mass.

In a case where the water-soluble ethylenically unsaturated monomer has an acid group, as in the case such as (meth)acrylic acid or 2-(meth)acrylamide-2-methylpropanesulfonic acid, the acid group previously neutralized with an alkaline neutralizing agent may be used, as occasion demands. The alkaline neutralizing agent as mentioned above includes, but not particularly limited to, alkaline metal salts such as sodium hydroxide and potassium hydroxide; ammonia, and the like.

These alkaline neutralizing agents especially may be used in the state of aqueous solutions in order to simplify the neutralization procedure. The above-mentioned alkaline neutralizing agents may be used alone or in combination of two or more kinds.

The neutralization degree to the entire acid groups of the water-soluble ethylenically unsaturated monomer with the alkaline neutralizing agent is, but not particularly limited to, usually preferably from 10 to 100% by mol, and more preferably from 30 to 80% by mol, in order to increase an osmotic pressure of the resulting water-absorbent resin, thereby increasing water-absorption properties, and not to cause some disadvantages in safety or the like caused by the presence of an excess alkaline neutralizing agent.

The petroleum hydrocarbon dispersion medium includes, for example, aliphatic hydrocarbons having from 6 to 8 carbon atoms such as n-hexane, n-heptane, 2-methylhexane, 3-methylhexane, 2,3-dimethylpentane, 3-ethylpentane, and n-octane; alicyclic hydrocarbons such as cyclohexane, methylcyclohexane, cyclopentane, methylcyclopentane, trans-1,2-dimethylcyclopentane, cis-1,3-dimethylcyclopentane, and trans-1,3-dimethylcyclopentane; aromatic hydrocarbons such as benzene, toluene, and xylene; and the like. These petroleum hydrocarbon dispersion media may be used alone or in combination of two or more kinds. Among these petroleum hydrocarbon dispersion media, n-heptane and cyclohexane are preferably used, from the viewpoint of being readily industrially available, stable in quality and inexpensive. In addition, favorable results are obtained when using a commercially available Exxsol heptane (manufactured by ExxonMobile, containing 75 to 85% by mass of heptane and its isomeric hydrocarbons) and the like as an example of a mixture of the above-mentioned petroleum hydrocarbon dispersion media.

The petroleum hydrocarbon dispersion medium is usually used in an amount of preferably from 50 to 600 parts by mass, and more preferably from 100 to 550 parts by mass, based on 100 parts by mass of the water-soluble ethylenically unsaturated monomer, from the viewpoint of homogeneously dispersing the water-soluble ethylenically unsaturated monomer, thereby facilitating the control of a polymerization temperature.

The radical polymerization initiator includes, for example, persulfates such as potassium persulfate, ammonium persulfate, and sodium persulfate; peroxides such as hydrogen peroxide; azo compounds such as 2,2'-azobis(2-amidinopropane)dihydrochloride, 2,2'-azobis[N-(2-carboxyethyl)-2-methylpropiondiamine]tetrahydrate, 2,2'-azobis(1-imino-1-pyrrolidino-2-methylpropane)dihydrochloride, 2,2'-azobis[2-methyl-N-(2-hydroxyethyl)-propionamide]; and the like. Among them, potassium persulfate, ammonium persulfate, sodium persulfate, and 2,2'-azobis(2-amidinopropane)dihydrochloride are preferred, from the viewpoint of being easily available and easily handled. These radical polymerization initiators may be used alone or in combination of two or more kinds.

The radical polymerization initiator is usually used in an amount of preferably from 0.00005 to 0.01 mol, based on 1 mol of the water-soluble ethylenically unsaturated monomer, from the viewpoint of shortening the time of the polymerization reaction and preventing an abrupt polymerization reaction.

Here, the above-mentioned radical polymerization initiator can be used as a redox polymerization initiator together with a reducing agent such as sodium sulfite, sodium hydrogensulfite, ferrous sulfate, or L-ascorbic acid.

In addition, in order to control the water-absorbent properties of the water-absorbent resin, a chain transfer agent may be added thereto. The chain transfer agent as mentioned above includes hypophosphites, thiols, thiolic acids, secondary alcohols, amines, and the like.

In the present invention, a crosslinking agent may be optionally used, when the water-soluble ethylenically unsaturated monomer is subjected to the reversed phase suspension polymerization. As the crosslinking agent (hereinafter referred to "internal-crosslinking agent") mentioned above, for example, a compound having two or more polymerizable unsaturated groups can be used but not particularly limited thereto. Specific examples of the compound as mentioned above includes, di- or tri(meth)acrylic esters of polyols such as (poly)ethylene glycol (in the present specification, for example, "polyethylene glycol" and "ethylene glycol" may be together expressed as "(poly)ethylene glycol"; hereinafter referred to the same), (poly)propylene glycol, trimethylolpropane, glycerol polyoxyethylene glycol, polyoxypropylene glycol, and (poly)glycerol; unsaturated polyesters obtained by reacting the above-mentioned polyols with unsaturated acids such as maleic acid and fumaric acid; bisacrylamides such as N,N'-methylenebis(meth)acrylamide; di- or tri(meth)acrylate esters obtained by reacting a polyepoxide with (meth)acrylic acid; carbamyl esters of di(meth)acrylic acid obtained by reacting a polyisocyanate such as tolylene diisocyanate or hexamethylene diisocyanate with hydroxyethyl (meth)acrylate; allylated starch, allylated cellulose, diallyl phthalate, N,N',N''-triallyl isocyanurate, divinylbenzene, and the like.

As the internal-crosslinking agent, in addition to the compound having two or more polymerizable unsaturated groups as mentioned above, a compound having two or more other reactive functional groups may be used. The internal-crosslinking agent described above can be exemplified by glycidyl group-containing compounds such as (poly)ethylene glycol diglycidyl ether, (poly)propylene glycol diglycidyl ether and (poly)glycerol diglycidyl ether; (poly)ethylene glycol, (poly)propylene glycol, (poly)glycerol, pentaerythritol, ethylenediamine, polyethyleneimine, glycidyl (meth)acrylate, and the like. These internal-crosslinking agents may be used alone or in combination of two or more kinds.

The internal-crosslinking agent may be added to a dispersion medium and used, and it is preferable that the internal-crosslinking agent is added to the above-mentioned monomer and used in order to more efficiently exhibit an effect by the internal-crosslinking agent.

When the internal-crosslinking agent is used, the internal-crosslinking agent is used in an amount of preferably from 0.0000001 to 0.01 mol, and more preferably from 0.000001 to 0.005 mol, based on 1 mol of the water-soluble ethylenically unsaturated monomer, in order to sufficiently enhance the water-absorption properties of the water-absorbent resin obtained.

In a reversed phase suspension polymerization, a thickener may be added to the water-soluble ethylenically unsaturated monomer in order to adjust its particle size. The thickener includes, for example, hydroxyethyl cellulose, hydroxypropyl cellulose, methyl cellulose, carboxymethyl cellulose, polyacrylic acid, (partially) neutralized polyacrylic acid, and the like.

The reaction temperature for the polymerization reaction differs depending upon the radical polymerization initiator to be used. Usually, the reaction temperature is preferably from 20° to 110° C., and more preferably from 40° to 90° C., from the viewpoint of quickly progressing the polymerization and shortening the polymerization time, thereby increasing productivity, and at the same time more easily removing heat of polymerization, to smoothly carry out the reaction. The reaction time is usually preferably from 0.1 to 4 hours or so.

In the present invention, the reversed phase suspension polymerization reaction can be carried out in two or more multi-steps. In other words, two or more multi-steps polymerization can be carried out by subjecting to a reversed phase suspension polymerization as mentioned above, thereafter cooling the reaction mixture of the polymerization, further adding water-soluble ethylenically unsaturated monomer thereto, and subjecting to a reversed phase suspension polymerization reaction. In two or more multi-steps polymerization, the particle size of the water-absorbent resin can be made larger by agglomerating the particles obtained in the first-step suspension polymerization, so that it is easier to obtain an appropriate particle size suitable for hygienic materials.

The cooling temperature of the above-mentioned reaction mixture of the first-step polymerization is, but not particularly limited to, for example, preferably from 5° to 40° C. or so, and more preferably 10° to 30° C. A time period needed for cooling the reaction mixture of the polymerization is not particularly limited.

In the reversed phase suspension polymerization in each of the second and subsequent steps, a reversed phase suspension polymerization can be carried out under the conditions similar to the above-mentioned method by adding a radical polymerization initiator and optionally an internal-crosslinking agent, in addition to the water-soluble ethylenically unsaturated monomer, within the range of a molar ratio of each component to the above-mentioned water-soluble ethylenically unsaturated monomer, based on the amount of the water-soluble ethylenically unsaturated monomer to be added during the reversed phase suspension polymerization in each of the second and subsequent steps.

It is preferable that the water-absorbent resin obtained by the reversed phase suspension polymerization of the present invention has a median particle size of usually within the range of from 20 to 800 μm. Incidentally, in order to suitably use the resin in the hygienic materials, the median particle size is more preferably from 60 to 700 μm, and even more preferably from 80 to 600 μm, from the viewpoint of favorably keeping flowability as a powder, and keeping the texture of hygienic materials soft.

In the present invention, it is preferable that a crosslinking agent is added to carry out post-crosslinking after the termination of the step of a reversed phase suspension polymerization of the water-soluble ethylenically unsaturated monomer. After the reversed phase suspension polymerization, a compound having a plurality of functional groups capable of reacting with a carboxyl group can be added as a crosslinking agent (hereinafter referred to "post-crosslinking agent") and subjected to a crosslinking treatment near the surface of the water-absorbent resin, thereby obtaining a water-absorbent resin having an excellent water-absorption capacity under load and the like. Further, an embodiment including the step of carrying out a reversed phase suspension polymerization reaction in two or more multi-steps, including adding a post-crosslinking agent, and subjecting to post-crosslinking after the termination of the step of the reversed phase suspension polymerization of the water-soluble ethylenically unsaturated monomer is more preferred, from the viewpoint of water-absorption capacity of the obtained water-absorbent resin.

The post-crosslinking agent as mentioned above includes compounds having two or more reactive functional groups. Examples thereof include polyols such as ethylene glycol, propylene glycol, 1,4-butanediol, trimethylolpropane, glycerol, polyoxyethylene glycol, polyoxypropylene glycol, and polyglycerol; polyglycidyl compounds such as (poly)ethylene glycol diglycidyl ether, (poly)ethylene glycol triglycidyl ether, (poly)glycerol diglycidyl ether, (poly)glycerol triglycidyl ether, (poly)propylene glycol polyglycidyl ether, and (poly)glycerol polyglycidyl ether; haloepoxy compounds such as epichlorohydrin, epibromohydrin, and a-methylepichlorohydrin; compounds having two or more reactive functional groups such as isocyanate compounds such as 2,4-tolylene diisocyanate, and hexamethylene diisocyanate; oxetane compounds such as 3-methyl-3-oxetanemethanol, 3-ethyl-3-oxetanemethanol, 3-butyl-3-oxetanemethanol, 3-methyl-3-oxetanethanol, 3-ethyl-3-oxetanethanol, and 3-butyl-3-oxetanethanol; oxazoline compounds such as 1,2-ethylenebis oxazoline; carbonate compounds such as ethylene carbonate; and the like. Among them, polyglycidyl compounds such as (poly)ethylene glycol diglycidyl ether, (poly)ethylene glycol triglycidyl ether, (poly)glycerol diglycidyl ether, (poly)glycerol triglycidyl ether, (poly)propylene glycol polyglycidyl ether, and (poly)glycerol polyglycidyl ether are preferred. These post-crosslinking agents may be used alone or in combination of two or more kinds.

The post-crosslinking agent is used in an amount of preferably from 0.00005 to 0.01 mol, and of more preferably from 0.0001 to 0.005 mol, based on 1 mol of a total amount of the water-soluble ethylenically unsaturated monomer used in the reversed phase suspension polymerization, from the viewpoint of appropriately enhancing a crosslinking density near the surface of the water-absorbent resin without lowering water-retention capacity of the resulting water-absorbent resin, thereby increasing water-absorption capacity under load.

The timing of addition of the post-crosslinking agent may be any time after the termination of the polymerization of the water-soluble ethylenically unsaturated monomer, but not particularly limited. The post-crosslinking agent is added in the presence of water preferably in an amount within the range of from 1 to 400 parts by mass, more preferably in the presence of water in an amount within the range of from 5 to 200 parts by mass, and even more preferably in the presence of water in an amount within the range of from 10 to 100 parts by mass, based on 100 parts by mass of a total amount of the water-soluble ethylenically unsaturated monomer. As described above, by controlling the amount of water upon addition of the post-crosslinking agent, the crosslinking is provided more preferably near the surface of the water-absorbent resin, whereby the water-absorbent resin having an excellent water-absorption capacity under load can be obtained.

As a method of adding a post-crosslinking agent, the post-crosslinking agent may be added directly, or may be added in the form of an aqueous solution. Also, a hydrophilic organic solvent may be used, as occasion demands, as a solvent. This hydrophilic organic solvent includes, for example, lower alcohols such as methyl alcohol, ethyl alcohol, n-propyl alcohol, isopropyl alcohol, and propylene glycol; ketones such as acetone and methyl ethyl ketone; ethers such as diethyl ether, dioxane, and tetrahydrofuran; amides such as N,N-dimethylformamide; sulfoxides such as dimethyl sulfoxide; and the like. These hydrophilic organic solvents may be used alone, or in a combination of two or more kinds, or in a mixed solvent with water.

The temperature during the post-crosslinking reaction is preferably from 50° to 250° C., more preferably from 60° to 180° C., even more preferably from 60° to 140° C., and even more preferably from 70° to 120° C. In addition, the reaction time of the above-mentioned post-crosslinking differs depending upon a reaction temperature, kinds and amount of the post-crosslinking agent, and the like, so that the reaction time cannot be unconditionally determined. The reaction time is usually preferably from 1 to 300 minutes or so, and more preferably from 5 to 200 minutes.

In the present invention, the drying step may be carried out at a normal pressure or under a reduced pressure, or the drying step may be carried out under a gas stream of nitrogen or the like, in order to increase drying efficiency. In a case where the drying step is carried out at a normal pressure, the drying temperature is preferably from 70° to 250° C., more preferably from 80° to 180° C., even more preferably from 80° to 140° C., and even more preferably from 90° to 130° C. In addition, in a case where the drying step is carried under a reduced pressure, the drying temperature is preferably from 60° to 100° C., and more preferably from 70° to 90° C.

The water content of the water-absorbent resin after drying is preferably 20% by mass or less, and more preferably from 3 to 15% by mass, from the viewpoint of flowability as a powder.

The water-absorbent resin of the present invention can be blended with a known additive such as a lubricant, a deodorant, an antibacterial agent, an antioxidant, or a degradation inhibitor of swollen gel, depending upon the purpose.

The water-absorbent resin of the present invention obtained as described above has a high water-retention capacity, a high water-absorption capacity under load and an excellent water-absorption rate, and further has an excellent flowability under moisture absorption, so that the resin is suitably used in hygienic materials.

Here, the water-retention capacity of saline solution, the water-absorption capacity of saline solution under load of 2.07 kPa, the water-absorption rate of saline solution, and the flow index under moisture absorption of the water-absorbent resin are measured according to the measurement methods described in Examples set forth below.

The water-absorbent resin of the present invention has a water-retention capacity of saline solution of preferably 25 g/g or more, more preferably 30 g/g or more, and even more preferably 35 g/g or more, from the viewpoint of increasing absorption capacity, when used in a hygienic material.

The water-absorbent resin of the present invention has a water-absorption capacity of saline solution under load of 2.07 kPa of preferably 20 ml/g or more, more preferably 25 ml/g or more, and even more preferably 30 ml/g or more, from the viewpoint of absorbing a liquid even in the case of under load, when used in a hygienic material.

The water-absorbent resin of the present invention has a water-absorption rate of saline solution of preferably 50 seconds or less, more preferably 40 seconds or less, and even more preferably 30 seconds or less, from the viewpoint of quickly absorbing a liquid, thereby preventing leakage, when used in a hygienic material.

The water-absorbent resin of the present invention has a flow index under moisture absorption of preferably 70% or more, more preferably 80% or more, and even more preferably 90% or more, from the viewpoint of having favorable handling ability of the water-absorbent resin, thereby making the particles less likely to firmly adhere to an internal of a machine for producing a hygienic material or the like, for example, an inner wall of a supplying hopper of the water-absorbent resin, an internal of a feeder, a metal mesh on which absorbent materials are laminated, or the like.

EXAMPLES

The present invention will be specifically described hereinbelow by Examples, without intending to limit the scope of the present invention thereto.

Example 1

A cylindrical round bottomed separable flask having an inner diameter of 100 mm, equipped with a reflux condenser, a dropping funnel, a nitrogen gas inlet tube, and a stirrer having two steps of stirring blades having 4 inclined paddle blades with a blade diameter of 50 mm was furnished. This flask was charged with 321 g of n-heptane, and 0.92 g of a polyoxyethylene stearyl ether stearate having an HLB value of 4 (Nihon Emulsion Co., Ltd., EMALEX SWS-4) and 0.92 g of a maleic anhydride-modified ethylene-propylene copolymer (Mitsui Chemicals, Inc., Hi-wax 1105A) were added thereto. The temperature was raised to 80° C. to dissolve the surfactant, and thereafter the solution was cooled to 55° C.

On the other hand, a 500 ml-Erlenmeyer flask was charged with 92 g (1.03 mol) of an 80.5% by mass aqueous solution of acrylic acid, 51.2 g of ion-exchanged water and 0.28 g of hydroxyethyl cellulose (Sumitomo Seika Chemicals Co., Ltd., AW-15F), and 102.9 g of a 30.0% by mass aqueous sodium hydroxide was added dropwise thereto with cooling from external to neutralize 75% by mol of the acrylic acid. Thereafter, 0.11 g (0.41 mmol) of potassium persulfate and 9.2 mg (0.053 mmol) of ethylene glycol diglycidyl ether were added thereto to dissolve, to prepare an aqueous monomer solution.

The above-mentioned aqueous monomer solution was added to the above-mentioned separable flask, and the flask was kept at 35° C. for 30 minutes while the internal of the system was replaced with nitrogen. Thereafter, the flask was immersed in a water bath kept at 70° C., and the polymerization was carried out for 30 minutes, thereby giving a reaction mixture of the polymerization.

Next, the above-mentioned reaction mixture of the polymerization was heated with an oil bath kept at 125° C., and water and n-heptane were subjected to azeotropic distillation to remove 126.2 g of water to the external of the system, while refluxing n-heptane. Thereafter, 3.68 g (0.42 mmol) of a 2% by mass aqueous solution of ethylene glycol diglycidyl ether was added thereto, and the mixture was kept at 80° C. for 2 hours. Subsequently, the reaction mixture was heated with an oil bath kept at 120° C., and the dispersion medium and water were removed to the external of the system by distillation. The reaction mixture was then dried under a nitrogen gas stream, to give 100.8 g of a spherical water-absorbent resin.

Example 2

The same procedures were carried out under the same conditions as in Example 1 except that the surfactant was changed to 0.92 g of a polyoxyethylene stearyl ether stearate having an HLB value of 5 (Nihon Emulsion Co., Ltd., EMALEX SWS-6), to give 98.3 g of a spherical water-absorbent resin.

Example 3

The same procedures were carried out under the same conditions as in Example 1 except that the surfactant was changed to 0.92 g of a polyoxyethylene stearyl ether stearate having an HLB value of 6 (Nihon Emulsion Co., Ltd., EMALEX SWS-9), to give 103.7 g of a spherical water-absorbent resin.

Example 4

The same procedures were carried out under the same conditions as in Example 1 except that the surfactant was changed to 0.92 g of a polyoxyethylene stearyl ether stearate having an HLB value of 7 (Nihon Emulsion Co., Ltd., EMALEX SWS-10) and further that the amount of the water removed to the external of the system was changed to 128 g, to give 108.1 g of a spherical water-absorbent resin.

Example 5

The same procedures were carried out under the same conditions as in Example 4 except that the surfactant was changed to 0.92 g of a polyoxyethylene stearyl ether stearate having an HLB value of 8 (Nihon Emulsion Co., Ltd., EMALEX SWS-12), to give 107.0 g of a spherical water-absorbent resin.

Example 6

A cylindrical round bottomed separable flask having an inner diameter of 100 mm, equipped with a reflux condenser, a dropping funnel, a nitrogen gas inlet tube, and a stirrer having two steps of stirring blades having 4 inclined paddle blades with a blade diameter of 50 mm was furnished. This flask was charged with 321 g of n-heptane, and 0.92 g of a polyoxyethylene stearyl ether stearate having an HLB value of 5 (Nihon Emulsion Co., Ltd., EMALEX SWS-6) and 0.92 g of a maleic anhydride-modified ethylene-propylene copolymer (Mitsui Chemicals, Inc., Hi-wax 1105A) were added thereto. The temperature was raised to 80° C. to dissolve the surfactant, and thereafter the solution was cooled to 55° C.

On the other hand, a 500 ml-Erlenmeyer flask was charged with 92 g (1.03 mol) of an 80.5% by mass aqueous solution of acrylic acid, 51.2 g of ion-exchanged water and 0.28 g of hydroxyethyl cellulose (Sumitomo Seika Chemicals Co., Ltd., AW-15F), and 102.9 g of a 30.0% by mass aqueous sodium hydroxide was added dropwise thereto with cooling from external to neutralize 75% by mol of the acrylic acid. Thereafter, 0.11 g (0.41 mmol) of potassium persulfate and 9.2 mg (0.053 mmol) of ethylene glycol diglycidyl ether were added thereto to dissolve, to prepare an aqueous monomer solution for the first step.

The above-mentioned aqueous monomer solution was added to the above-mentioned separable flask, and the flask was kept at 35° C. for 30 minutes while the internal of the system was replaced with nitrogen. Thereafter, the flask was immersed in a water bath kept at 70° C., and the polymerization was carried out for 30 minutes, thereby giving a reaction mixture of the first-step polymerization.

On the other hand, another 500 ml-Erlenmeyer flask was charged with 110.4 g (1.23 mol) of an 80.5% by mass aqueous solution of acrylic acid and 26.3 g of ion-exchanged water, and 123.4 g of a 30.0% by mass aqueous sodium hydroxide was added dropwise thereto with cooling from external to neutralize 75% by mol of the acrylic acid. Thereafter, 0.13 g (0.48 mmol) of potassium persulfate and 11.0 mg (0.063 mmol) of ethylene glycol diglycidyl ether were added thereto to dissolve, to prepare an aqueous monomer solution for the second step.

The above-mentioned reaction mixture of the first-step polymerization was cooled to 25° C. The above-mentioned aqueous monomer solution for the second step was added to the internal of the system, and the mixture was kept for 30 minutes while the system was replaced with nitrogen.

The flask was again immersed in a water bath kept at 70° C. to raise the temperature, and the polymerization was carried out for 30 minutes, thereby giving a reaction mixture of the second-step polymerization.

Next, the above-mentioned reaction mixture of the polymerization was heated with an oil bath kept at 120° C., and water and n-heptane were subjected to azeotropic distillation to remove 249 g of water to the external of the system, while refluxing n-heptane. Thereafter, 3.96 g (0.45 mmol) of a 2% by mass aqueous solution of ethylene glycol diglycidyl ether was added thereto. Subsequently, the reaction mixture was heated with an oil bath kept at 120° C., and the dispersion medium and water were removed to the external of the system by distillation. The reaction mixture was then dried under a nitrogen gas stream, to give 203.9 g of a water-absorbent resin in the form of agglomerated spherical particles.

Example 7

A cylindrical round bottomed separable flask having an inner diameter of 100 mm, equipped with a reflux condenser, a dropping funnel, a nitrogen gas inlet tube, and a stirrer having two steps of stirring blades having 4 inclined paddle blades with a blade diameter of 50 mm was furnished. This flask was charged with 321 g of n-heptane, and 0.92 g of a polyoxyethylene stearyl ether stearate having an HLB value of 7 (Nihon Emulsion Co., Ltd., EMALEX SWS-10) was added thereto. The temperature was raised to 80° C. to dissolve the surfactant, and thereafter the solution was cooled to 55° C.

On the other hand, a 500 ml-Erlenmeyer flask was charged with 92 g (1.03 mol) of an 80.5% by mass aqueous solution of acrylic acid, 51.2 g of ion-exchanged water and 0.28 g of hydroxyethyl cellulose (Sumitomo Seika Chemicals Co., Ltd., AW-15F), and 102.9 g of a 30.0% by mass aqueous sodium hydroxide was added dropwise thereto with cooling from external to neutralize 75% by mol of the acrylic acid. Thereafter, 0.11 g (0.41 mmol) of potassium persulfate and 9.2 mg (0.053 mmol) of ethylene glycol diglycidyl ether were added thereto to dissolve, to prepare an aqueous monomer solution for the first step.

The above-mentioned aqueous monomer solution was added to the above-mentioned separable flask, and the flask was kept at 35° C. for 30 minutes while the internal of the system was replaced with nitrogen. Thereafter, the flask was immersed in a water bath kept at 70° C. to raise the temperature, and the polymerization was carried out for 30 minutes, thereby giving a reaction mixture of the first-step polymerization.

On the other hand, another 500 ml-Erlenmeyer flask was charged with 128.2 g (1.43 mol) of an 80.5% by mass aqueous solution of acrylic acid and 30.5 g of ion-exchanged water, and 143.3 g of a 30.0% by mass aqueous sodium hydroxide was added dropwise thereto with cooling from external to neutralize 75% by mol of the acrylic acid. Thereafter, 0.15 g (0.55 mmol) of potassium persulfate and 12.8 mg (0.073 mmol) of ethylene glycol diglycidyl ether were added thereto to dissolve, to prepare an aqueous monomer solution for the second step.

The above-mentioned reaction mixture of the first-step polymerization was cooled to 25° C. The above-mentioned aqueous monomer solution for the second step was added to the internal of the system, and the mixture was kept for 30 minutes while the system was replaced with nitrogen.

The flask was again immersed in a water bath kept at 70° C. to raise the temperature, and the polymerization was carried out for 30 minutes, thereby giving a reaction mixture of the second-step polymerization.

Next, the reaction mixture was heated with an oil bath kept at 120° C., and water and n-heptane were subjected to azeotropic distillation to remove 267.3 g of water to the external of the system, while refluxing n-heptane. Thereafter, 3.96 g (0.45 mmol) of a 2% by mass aqueous solution of ethylene glycol diglycidyl ether was added thereto, and the reaction mixture was kept at 80° C. for 2 hours. Subsequently, the reaction mixture was heated with an oil bath kept at 120° C., and the dispersion medium and water were removed to the external of the system by distillation. The reaction mixture was then dried under a nitrogen gas stream, to give 201.0 g of a water-absorbent resin in the form of agglomerated spherical particles.

Example 8

The same procedures were carried out under the same conditions as in Example 6 except that the surfactant was changed to 0.92 g of a polyoxyethylene cetyl ether stearate having an HLB value of 7 (Nihon Emulsion Co., Ltd., EMALEX CWS-10), to give 202.4 g of a water-absorbent resin in the form of agglomerated spherical particles.

Comparative Example 1

The same procedures were carried out under the same conditions as in Example 1 except that the surfactant was changed to 0.92 g of a sucrose stearate having an HLB value of 3 (Mitsubishi-Kagaku Foods Corporation, Ryoto sugar ester S-370) and further that the amount of water removed to the external of the system was changed to 116 g, to give 98.0 g of a spherical water-absorbent resin.

Comparative Example 2

A cylindrical round bottomed separable flask having an inner diameter of 100 mm, equipped with a reflux condenser, a dropping funnel, a nitrogen gas inlet tube, and a stirrer having two steps of stirring blades having 4 inclined paddle blades with a blade diameter of 50 mm was furnished. This flask was charged with 321 g of n-heptane, and 0.92 g of a sucrose stearate having an HLB value of 3 (Mitsubishi-Kagaku Foods Corporation, Ryoto sugar ester S-370) and 0.92 g of a maleic anhydride-modified ethylene-propylene copolymer (Mitsui Chemicals, Inc., Hi-wax 1105A) were added thereto. The temperature was raised to 80° C. to dissolve the surfactant, and thereafter the solution was cooled to 55° C.

On the other hand, a 500 ml-Erlenmeyer flask was charged with 92 g (1.03 mol) of an 80.5% by mass aqueous solution of acrylic acid, 51.2 g of ion-exchanged water and 0.28 g of hydroxyethyl cellulose (Sumitomo Seika Chemicals Co., Ltd., AW-15F), and 102.9 g of a 30.0% by mass aqueous sodium hydroxide was added dropwise thereto with cooling from external to neutralize 75% by mol of the acrylic acid. Thereafter, 0.11 g (0.41 mmol) of potassium persulfate and 9.2 mg (0.053 mmol) of ethylene glycol diglycidyl ether were added thereto to dissolve, to prepare an aqueous monomer solution for the first step.

The above-mentioned aqueous monomer solution was added to the above-mentioned separable flask, and the flask was kept at 35° C. for 30 minutes while the internal of the system was replaced with nitrogen. Thereafter, the flask was immersed in a water bath kept at 70° C. to raise the temperature, and the polymerization was carried out for 30 minutes, thereby giving a reaction mixture of the first-step polymerization.

On the other hand, another 500 ml-Erlenmeyer flask was charged with 128.2 g (1.43 mol) of an 80.5% by mass aqueous solution of acrylic acid and 30.5 g of ion-exchanged water, and 143.3 g of a 30.0% by mass aqueous sodium hydroxide was added dropwise thereto with cooling from external to neutralize 75% by mol. Thereafter, 0.15 g (0.55 mmol) of potassium persulfate and 12.8 mg (0.073 mmol) of ethylene glycol diglycidyl ether were added thereto to dissolve, to prepare an aqueous monomer solution for the second step.

The above-mentioned reaction mixture of the first-step polymerization was cooled to 28° C. The above-mentioned aqueous monomer solution for the second step was added to the internal of the system, and the mixture was kept for 30 minutes while the system was replaced with nitrogen.

The flask was again immersed in a water bath kept at 70° C. to raise the temperature, and the polymerization was carried out for 30 minutes, thereby giving a reaction mixture of the second-step polymerization.

Next, the reaction mixture was heated with an oil bath kept at 120° C., and water and n-heptane were subjected to azeotropic distillation to remove 267.8 g of water to the external of the system, while refluxing n-heptane. Thereafter, 3.96 g (0.45 mmol) of a 2% by mass aqueous solution of ethylene glycol diglycidyl ether was added thereto. Subsequently, the reaction mixture was heated with an oil bath kept at 120° C., and the dispersion medium and water were removed to the external of the system by distillation. The reaction mixture was dried under a nitrogen gas stream, to give 227.4 g of a water-absorbent resin in the form of agglomerated spherical particles.

Comparative Example 3

A cylindrical round bottomed separable flask having an inner diameter of 100 mm, equipped with a reflux condenser, a dropping funnel, a nitrogen gas inlet tube, and a stirrer having two steps of stirring blades having 4 inclined paddle blades with a blade diameter of 50 mm was furnished. This flask was charged with 321 g of n-heptane, and 0.92 g of a sucrose stearate having an HLB value of 3 (Mitsubishi-Kagaku Foods Corporation, Ryoto sugar ester S-370) and 0.92 g of a maleic anhydride-modified ethylene-propylene copolymer (Mitsui Chemicals, Inc., Hi-wax 1105A) were added thereto. The temperature was raised to 80° C. to dissolve the surfactant, and thereafter the solution was cooled to 55° C.

On the other hand, a 500 ml-Erlenmeyer flask was charged with 92 g (1.03 mol) of an 80.5% by mass aqueous solution of acrylic acid, 51.2 g of ion-exchanged water and 0.28 g of hydroxyethyl cellulose (Sumitomo Seika Chemicals Co., Ltd., AW-15F), and 102.9 g of a 30.0% by mass aqueous sodium hydroxide was added dropwise thereto with cooling from external to neutralize 75% by mol of the acrylic acid. Thereafter, 0.11 g (0.41 mmol) of potassium persulfate and 27.6 mg (0.16 mmol) of ethylene glycol diglycidyl ether were added thereto to dissolve, to prepare an aqueous monomer solution for the first step.

The above-mentioned aqueous monomer solution was added to the above-mentioned separable flask, and the flask was kept at 35° C. for 30 minutes while the internal of the system was replaced with nitrogen. Thereafter, the flask was immersed in a water bath kept at 70° C. to raise the temperature, and the polymerization was carried out for 30 minutes, thereby giving a reaction mixture of the first-step polymerization.

On the other hand, another 500 ml-Erlenmeyer flask was charged with 119.1 g (1.33 mol) of an 80.5% by mass aqueous solution of acrylic acid and 30.5 g of ion-exchanged water, and 133.2 g of a 30.0% by mass aqueous sodium hydroxide was added dropwise thereto with cooling from external to neutralize 75% by mol. Thereafter, 0.14 g (0.52 mmol) of potassium persulfate and 35.7 mg (0.20 mmol) of ethylene glycol diglycidyl ether were added thereto to dissolve, to prepare an aqueous monomer solution for the second step.

The above-mentioned reaction mixture of the first-step polymerization was cooled to 28° C. The above-mentioned aqueous monomer solution for the second step was added to the internal of the system, and the mixture was kept for 30 minutes while the system was replaced with nitrogen.

The flask was again immersed in a water bath kept at 70° C. to raise the temperature, and the polymerization was carried out for 30 minutes, thereby giving a reaction mixture of the second-step polymerization.

Next, the reaction mixture was heated with an oil bath kept at 120° C., and water and n-heptane were subjected to azeotropic distillation to remove 259.9 g of water to the external of the system, while refluxing n-heptane. Thereafter, 11.0 g (1.26 mmol) of a 2% by mass aqueous solution of ethylene glycol diglycidyl ether was added thereto. Subsequently, the reaction mixture was heated with an oil bath kept at 120° C., and the dispersion medium and water were removed to the external of the system by distillation. The reaction mixture was then dried under a nitrogen gas stream, to give 217.1 g of a water-absorbent resin in the form of agglomerated spherical particles.

With regard to the water-absorbent resins of Examples 1 to 8 and Comparative Examples 1 to 3, (1) water-retention capacity of saline solution, (2) water-absorption capacity of saline solution under load of 2.07 kPa, (3) water-absorption rate of saline solution, (4) flow index under moisture absorption, (5) median particle size, and (6) water content were measured according to the following procedures. The results are shown in Table 1.

(1) Water-Retention Capacity of Saline Solution

Five-hundred grams of a 0.9% by mass aqueous sodium chloride (saline solution) was weighed in a 500 mL beaker. The amount 2.0 g of a water-absorbent resin was added thereto, while stirring the solution at a rate of 600 r/min, to disperse so as not to cause an unswollen lump of the water-absorbent resin. Under the state of stirring, the dispersion was allowed to stand for 30 minutes, the water-absorbent resin was allowed to sufficiently swell. Thereafter, the dispersion was poured into a cotton bag (Cotton Broadcloth No. 60, width 100 mm×length 200 mm), and an upper part of the cotton bag was tied up with a rubber band. The cotton bag was dehydrated for 1 minute with a dehydrator, manufactured by Kokusan Enshinki Co., Ltd., product number: H-122, set to have a centrifugal force of 167 G. The mass Wa (g) of the cotton bag containing the swollen gel after dehydration was measured. The same procedures were carried out without adding a water-absorbent resin, and the empty mass Wb (g) of the cotton bag upon wetting was measured. The water-retention capacity was calculated from the following formula:

Water-Retention Capacity of Saline Solution (g/g)= [$Wa-Wb$] (g)/Mass of Water-Absorbent Resin (g)

(2) Water-Absorption Capacity of Saline Solution Under Load of 2.07 kPa

The water-absorption capacity of saline solution under load of 2.07 kPa of a water-absorbent resin was measured using a measurement apparatus X of which outline constitution was shown in the figure.

The apparatus X shown in the figure comprises a burette section 1, a lead tube 2, a measuring platform 3, and a measuring section 4 placed on the measuring platform 3.

The burette section 1 is connected with a rubber plug 14 on the top of a burette 10, and an air inlet tube 11 and a cock 12 at the bottom portion thereof, and further the air inlet tube 11 has a cock 13 at a top portion thereof. The lead tube 2 is attached between the burette section 1 and the measuring platform 3. The lead tube 2 has an inner diameter of 6 mm. A hole of a diameter of 2 mm is made at the central section of the measuring platform 3, and the lead tube 2 is connected thereto. The measuring section 4 has a cylinder 40, a nylon mesh 41 adhered to the bottom part of the cylinder 40, and a weight 42. The cylinder 40 has an inner diameter of 20 mm. The nylon mesh 41 has an opening of 75 μm (200 mesh), and the water-absorbent resin 5 is evenly spread over the nylon mesh 41 during the measurement. The weight 42 has a diameter of 19 mm and a mass of 59.8 g. This weight is placed on the water-absorbent resin 5, so that a load of 2.07 kPa can be applied to the water-absorbent resin 5.

Next, the measurement procedures will be described. The measurements are taken indoors at 25° C. First, the cock 12 and the cock 13 at the burette section 1 are closed, and a saline solution adjusted to 25° C. is poured from the top of the burette 10 and the top of the burette is plugged with the rubber plug 14. Thereafter, the cock 12 and the cock 13 at the burette section 1 are opened. Next, the height of the measuring platform 3 is adjusted so that the water level of the saline solution flowing out from the lead tube port at the central section of the measuring platform 3 is at the same height as the upper side of the measuring platform 3.

The amount 0.10 g of the water-absorbent resin 5 is evenly spread over the nylon mesh 41 in the cylinder 40, and the weight 42 is placed on the water-absorbent resin 5 to furnish the measuring section 4. Thereafter, the measuring section 4 is placed so that its center is in alignment with a lead tube port in the central section of the measuring platform 3.

The volume reduction of the saline solution in the burette 10 after 60 minutes passed from a time point at which bubbles are generated in the burette 10 from the air inlet tube 11 and the water-absorbent resin 5 starts to absorb water, i.e., the volume of the saline solution absorbed by the water-absorbent resin 5, Wc (ml), is read off. The water-absorption capacity of saline solution under load of 2.07 kPa of the water-absorbent resin 5 was obtained by the following formula.

Water-Absorption Capacity of Saline Solution under Load of 2.07 kPa (ml/g)=$Wc$ (ml)/Mass of Water-Absorbent Resin (g)

(3) Water-Absorption Rate of Saline Solution

The amount 50±0.01 g of saline solution at a temperature of 25°±0.2° C. was weighed out in a 100 mL beaker, and a magnetic stirrer bar (8 mmϕ)×30 mm, without a ring) was placed therein. A rotational speed was adjusted to be 600 r/min. Next, the water-absorbent resin was quickly added in an amount of 2.0±0.002 g to the above beaker, and the stopwatch was started at the same time of the termination of addition. The time period (seconds) from a point at which the water-absorbent resin absorbs the saline solution to a point of convergence of the vortex of the liquid surface was measured with a stopwatch, which was defined as water-absorption rate of saline solution.

(4) Flow Index under Moisture Absorption

The amount 5.0 g of the water-absorbent resin passing through a JIS standard sieve having an opening of 850 μm was evenly spread on a smooth aluminum plate (size: 120 mm×120 mm, thickness: 0.3 mm, mass: about 11 g). This sample was allowed to stand for 90 minutes in a thermohygrostat (NAGANO SCIENCE Co., Ltd., model: LH-20) controlled to the conditions of a temperature of 30°±1° C. and relative humidity of 80±5%, and the sample was allowed to absorb moisture. The mass (Wd) of the water-absorbent resin after moisture absorption was measured, and thereafter an aluminum plate was placed on a sieve having an opening of 1400 μm with a receiving tray, the side on which the water-absorbent resin was placed facing downward.

The sieves were placed with keeping a lid and subjected to tapping five times with a rotating and tapping shaker machine, and the mass (We) of the water-absorbent resin passing through the sieves was measured. The flow index under moisture absorption was calculated by the following formula.

Flow Index under Moisture Absorption (%)=(We/Wd)×100

(5) Median Particle Size

An amorphous silica (Sipernat 200, Degussa Japan) in an amount of 0.25 g as a lubricant was mixed with 50 g of a water-absorbent resin. The water-absorbent resin was allowed to pass through a JIS standard sieve having an opening of 250 μM, and a median particle size was measured using a combination of sieves of <α> in a case where the resin remaining on the sieves was in an amount of 50% by mass or more, or a combination of sieves of <β> in a case where the resin remaining on the sieves was in an amount of less than 50% by mass.

<α>

JIS standard sieves, a sieve having an opening of 850 μm, a sieve having an opening of 600 μm, a sieve having an opening of 500 μm, a sieve having an opening of 400 μm, a sieve having an opening of 300 μm, a sieve having an opening of 250 μm, a sieve having an opening of 150 μm, and a receiving tray were combined in order from the top.

<β>

JIS standard sieves, a sieve having an opening of 500 μm, a sieve having an opening of 250 μm, a sieve having an opening of 180 μm, a sieve having an opening of 150 μm, a sieve having an opening of 106 μm, a sieve having an opening of 75 μm, a sieve having an opening of 45 μm, and a receiving tray were combined in order from the top.

Fifty grams of the above-mentioned water-absorbent resin was placed on the uppermost sieve of the combined sieves, and shaken for 20 minutes with a rotating and tapping shaker machine to classify the resin.

After classification, the relationships between the opening of the sieve and an integral of a mass percentage of the water-absorbent resin remaining on the sieve were plotted on a logarithmic probability paper by calculating the mass of the water-absorbent resin remaining on each sieve as a mass percentage to an entire amount, and accumulating the mass percentages in order, starting from those having larger particle diameters. A particle diameter corresponding to a 50% by mass cumulative mass percentage was defined as a median particle size by joining the plots on the probability paper in a straight line.

(6) Water Content

The amount 2.0 g of the water-absorbent resin was precisely weighed out (Wg (g)) in an aluminum foil case (No. 8) of which constant weight was previously measured (Wf (g)). The above sample was dried for 2 hours with a hot-air dryer (manufactured by ADVANTEC) set at an internal temperature of 105° C. Thereafter, the dried sample was allowed to be cooled in a desiccator, and the mass Wh (g) after drying was measured. The water content of the water-absorbent resin was calculated from the following formula.

Water Content (% by Mass)=[(Wg−Wf)−(Wh−Wf)]/(Wg−Wf)×100

TABLE 1

|  | Water-Retention Capability of Saline Solution (g/g) | Water-Absorption Capability of Saline Solution under Load of 2.07 kPa (ml/g) | Water-Absorption Rate of Saline Solution (sec) | Flow Index under Moisture Absorption | Median Particle Size (μm) | Water Content (%) |
|---|---|---|---|---|---|---|
| Ex. 1 | 43 | 39 | 23 | 100 | 102 | 4.0 |
| Ex. 2 | 47 | 34 | 26 | 100 | 125 | 3.7 |
| Ex. 3 | 40 | 37 | 18 | 99 | 103 | 4.7 |
| Ex. 4 | 44 | 31 | 17 | 97 | 115 | 3.1 |
| Ex. 5 | 41 | 27 | 11 | 74 | 90 | 3.4 |
| Ex. 6 | 41 | 25 | 39 | 97 | 498 | 4.3 |
| Ex. 7 | 37 | 27 | 29 | 99 | 693 | 6.5 |
| Ex. 8 | 40 | 26 | 35 | 98 | 534 | 4.6 |
| Comp. Ex. 1 | 44 | 35 | 37 | 50 | 128 | 8.8 |
| Comp. Ex. 2 | 43 | 31 | 57 | 62 | 405 | 5.9 |
| Comp. Ex. 3 | 23 | 24 | 51 | 83 | 365 | 4.2 |

As is clear from the above results, in the production methods of Examples 1 to 8, the water-absorbent resins having high water-retention capacity (water-absorption capacity) and excellent water-absorption rate, and further having excellent flowability under moisture absorption were obtained.

On the other hand, in Comparative Examples, water-absorbent resins were one having high water-retention capacity but worsened flowability under moisture absorption (Comparative Example 1), one having slow water-absorption rate (Comparative Example 2), and one having excellent flowability under moisture absorption but low water-retention capacity (Comparative Example 3), so that the water-absorbent resins which can satisfy water-retention capacity, water-absorption rate, and flowability under moisture absorption at the same time could not be obtained.

Industrial Applicability

Since the water-absorbent resin obtained by the method of the present invention can enhance various properties such as absorption capacity and absorption rate of hygienic materials, and avoid some disadvantages possibly caused in the step of producing hygienic materials, the water-absorbent resin can be suitably used in hygienic materials such as sanitary napkins, incontinence pads and disposable diapers.

EXPLANATION OF NUMERICAL SYMBOLS

X measurement apparatus
1 burette section
10 burette
11 air inlet tube
12 cock
13 cock
14 rubber plug
2 lead tube
3 measuring platform
4 measuring section
40 cylinder
41 nylon mesh
42 weight
5 water-absorbent resin

The invention claimed is:

1. A method for producing a water-absorbent resin, the method comprising:
   subjecting a water-soluble ethylenically unsaturated monomer to a reversed phase suspension polymerization in a petroleum-based hydrocarbon dispersion medium in the presence of a radical polymerization initiator and a dispersion stabilizer,
   wherein an ether-ester type nonionic surfactant is used as the dispersion stabilizer, and said surfactant is at least one selected from the group consisting of polyoxyethylene cetyl ether stearate, polyoxyethylene stearyl ether stearate, polyoxyethylene lauryl ether stearate and polyoxyethylene lauryl ether isostearate.

2. The method according to claim 1, wherein the ether-ester type nonionic surfactant is combined with at least one compound selected from the group consisting of maleic anhydride-modified polyethylene, maleic anhydride-modified polypropylene, maleic anhydride-modified ethylene-propylene copolymer, oxidized polyethylene and ethylene-acrylic acid copolymer as the dispersion stabilizer.

3. The method according to claim 1, wherein the reversed phase suspension polymerization reaction is carried out in two or more multi-steps.

4. The method according to claim 1, further comprising:
   subsequent to termination of the reversed phase suspension polymerization, adding a post-crosslinking agent to carry out a post-crosslinking.

5. The method according to claim 1, wherein
   the reversed phase suspension polymerization reaction is carried out in two or more multi-steps, and
   subsequent to termination of the reversed phase suspension polymerization, the method further comprises adding a post-crosslinking agent to carry out a post-crosslinking.

6. A water-absorbent resin obtained by the method according to claim 1, wherein the water-absorbent resin has a water-retention capacity of saline solution of 25 g/g or more, a water-absorption rate of saline solution of 50 seconds or less, and a flow index under moisture absorption of 70% or more.

7. The method according to claim 2, wherein the reversed phase suspension polymerization reaction is carried out in two or more multi-steps.

8. The method according to claim 2, further comprising:
   subsequent to termination of the reversed phase suspension polymerization, adding a post-crosslinking agent to carry out a post-crosslinking.

* * * * *